United States Patent [19]

Sze et al.

[11] 3,965,194

[45] June 22, 1976

[54] PRODUCTION OF FORMALDEHYDE IN CARBON STEEL REACTORS

[75] Inventors: Morgan C. Sze, Upper Montclair; Harold Unger, Fort Lee, both of N.J.

[73] Assignee: The Lummus Company, Bloomfield, N.J.

[22] Filed: Oct. 19, 1973

[21] Appl. No.: 408,106

[52] U.S. Cl. .......................................... 260/603 HF
[51] Int. Cl.². ........................................ C07C 45/16
[58] Field of Search ............................. 260/603 HF

[56] References Cited
FOREIGN PATENTS OR APPLICATIONS
810,096    5/1951    Germany ..................... 260/603 HF

OTHER PUBLICATIONS

Takasaka, A., Chemical Abstracts, vol. 68, 62017y, 1968.

Hausler et al., Chemical Abstracts, vol. 74, 145297q, 1971.

Plesniak, S., Chemical Abstracts, vol. 63, 9553, 1965.

Walker, Formaldehyde, 3rd. Edit., pp. 97–99, 1964.

*Primary Examiner*—James O. Thomas, Jr.
*Assistant Examiner*—W. B. Lone
*Attorney, Agent, or Firm*—Marn & Jangarathis

[57] ABSTRACT

A carbon steel reactor can be used for producing formaldehyde from methanol by passivating the reactor with respect to formic acid production by treatment with either hydrogen sulfide in the absence of oxygen or a mixture of sulfur dioxide and oxygen.

11 Claims, No Drawings

PRODUCTION OF FORMALDEHYDE IN CARBON STEEL REACTORS

This invention relates to the production of formaldehyde. More particularly this invention relates to the production of formaldehyde by the oxidation of methanol in carbon steel reactors.

In the production of formaldehyde by the oxidation of methanol, stainless steel reactors have been required in order to avoid the production of formic acid, which is produced as a side product. In general, the formaldehyde product should not contain in excess of about 400 ppm. of formic acid. In attempting to use carbon steel reactors, the initial operation results in the production of formaldehyde product which contains formic acid in excess of such maximum tolerated quantities. Although the amount of formic acid produced decreases in due time to an acceptable value, in general, this time may involve ten or more weeks of operation which normally can not be tolerated.

An object of the present invention is to provide a process for pretreating carbon steel reactors for use in the production of formaldehyde.

Another object of the present invention is to produce formaldehyde in a carbon steel reactor with minimum production of formic acid.

These and other objects of the present invention should be apparent from reading the following description thereof.

In accordance with the present invention, a carbon steel reactor which is to be used for producing formaldehyde by the oxidation of methanol is passivated to minimize the production of formic acid byproduct by treating the surface of the reactor with a passivating amount of either a mixture of sulfur dioxide and oxygen or with hydrogen sulfide, in the absence of oxygen. The new iron surface which normally catalyzes the production of formic acid is passivated rapidly and the formaldehyde product produced by the oxidation of methanol in the reactor, subsequent to the treatment, contains acceptably low formic acid content; i.e., less than 400 ppm of formic acid.

In employing hydrogen sulfide as the treating agent for the passivaton of the carbon steel reactor, the carbon steel surface, prior to such treatment, is preferably in an oxidized state; i.e., there is an oxidized film surface. A clean carbon steel surface, such as is attained by acid pickling, is oxidized prior to the passivation treatment. In general, such oxidation may be effected by contacting the carbon steel surface with oxygen, generally as air, at a temperature and a time sufficient to effect such oxidation. In general, the temperature is from about 300°F. to about 800°F. and preferably about 500°F to about 650°F. and for a time from about 1 hour to about 4 hours. If the carbon steel is in an oxidized state, no pretreatment is required.

The treatment wth hydrogen sulfide is effected in the absence of free (molecular) oxygen. Accordingly, the reactor is generally purged of oxygen by passing a suitable inert gas, such as nitrogen, therethrough prior to treatment with hydrogen sulfide.

The treatment with hydrogen sulfide may be effected by completely filling the reactor with hydrogen sulfide to insure contact of all reactor surfaces. The carbon steel surfaces are maintained in contact with the hydrogen sulfide at a temperature and for a time sufficient to passivate the carbon steel with respect to the production of formic acid. In general, the treatment is effected at a temperature from about 300°F. to about 800°F., preferably from about 500°F. to about 650°F. The time required for passivation will vary depending on conditions employed. In general, the treatment is effected for at least about 0.5 hour, and most generally, from about 2 to about 24 hours. It is to be understood that the hereinabove described temperatures and times are not intended to limit the scope of the invention in that the selection of optimum times and temperatures are deemed to be within the scope of those skilled in the art from the teachings herein.

The hydrogen sulfide may be employed itself, or in admixture with an inert gas, such as nitrogen. If diluted, the hydrogen sulfide concentration is generally at least about 1.5%, by volume, i.e., the treatment may be effected with 1.5% to about 100%, by volume, hydrogen sulfide. It should be readily apparent that lower concentrations generally require longer treatment times and, accordingly, the use of concentrations of less than 1.5%, by volume, are also possible.

The passivation with hydrogen sulfide may be effected with the catalyst for the production of formaldehyde present in the reactor. In such a case, the hydrogen sulfide should be admixed with an inert gas, with the hydrogen sulfide concentration generally being no greater than about 14 volume percent in that the use of higher concentrations may be detrimental to the catalyst.

After the passivation with hydrogen sulfide, the reactor is preferably purged with an inert gas, such as nitrogen to assure that the reactor is purged of residual gases. Oxygen generally in the form of air, is then passed through the reactor. An elevated temperature may be used and the effluent gas tested for sulfur dioxide, which is produced by the oxidation of any sulfides which are present. The reactor may then be employed for the production of formaldehyde by the oxidation of methanol.

The carbon steel reactor may also be passivated with respect to the production of formic acid by treatment thereof with a gas containing passivating amounts of oxygen and sulfur dioxide. The volume ratio of oxygen to sulfur dioxide in the gas generally ranges from about 4:1 to about 40:1, with the passivating gas being most conveniently provided by adding sulfur dioxide to air in a concentration of from about 0.5% to about 5%, by volume. The air is preferably humidified by bubbling the air through water prior to admixture with sulfur dioxide.

The treatment with the mixture of sulfur dioxide and oxygen is effected at a temperature and for a time to passivate the carbon steel reactor surfaces with respect to the production of formic acid byproduct. In general, the temperature is from about 300°F. to about 800°F., and preferably from about 500°F. to about 650°F. The time required for effecting such passivation will vary depending on conditions employed. In general, the treatment is effected for at least 1 hour, and most generally from about 2 to about 24 hours.

As in the case of the treatment with hydrogen sulfide, the treatment with sulfur dioxide and oxygen may be effected with the catalyst present in the reactor.

Subsequent to the treatment, the reactor may be purged with oxygen, generally as air, to sweep out any remaining sulfur dioxide. The reaction may then be employed for the production of formaldehyde by the oxidation of methanol.

The formaldehyde is produced from methanol as known in the art. In brief, a mixture of methanol, water and free oxygen containing gas, generally in the form of air, in non-explosive proportions are passed through the reactor which includes a suitable methanol oxidation catalyst, such as, iron molybdate, or tungsten molybdate and is maintained at a temperature from about 500°F. to about 650°F. The details of the process are known in the art and, accordingly, no further details in this respect are needed for a full understanding of the present invention.

The invention will be further described with respect to the following examples, but the scope of the invention is not to be limited thereby. Unless otherwise indicated, all parts and percentages are by weight.

EXAMPLE I

A carbon steel reactor was packed with an iron-molybdate catalyst. The feed consisted of a gas mixture of the following composition:

|  | Vol. % |
|---|---|
| Air | 46.2 |
| Nitrogen | 41.1 |
| Methanol | 9.1 |
| Water | 3.6 |
|  | 100.0 |

The space velocity was 6000 hr.$^{-1}$. The reactor pressure was 2 inches of mercury and the reactor coolant bath temperature was 600°F.

The 50% formaldehyde product initially contained over 10,000 ppm. formic acid. After a few days operation the formic acid content was still in excess of 10,000 ppm.

EXAMPLE II

The reactor of Example I was then treated with a mixture of 1 volume percent sulfur dioxide in air for a period of 6½ hours. The reactor was then used for the production of formaldehyde as described in Example I. The 50 wt.% formaldehyde solution contained 200 ppm. formic acid.

The reactor was then treated for 2½ hours with 1 volume percent sulfur dioxide in air. Subsequent to this treatment the formic acid concentration was reduced to 80 ppm.

EXAMPLE III

A carbon steel reactor was packed with iron-molybdate catalyst. The feed consisted of a gas mixture of the following composition:

|  | Vol. % |
|---|---|
| Air | 44.0 |
| Nitrogen | 42.3 |
| Methanol | 9.9 |
| Water | 3.8 |
|  | 100.0 |

The space velocity was 5845 hr.$^{-1}$. The reactor pressure was 2 inches of mercury and the reactor coolant bath temperature was 600°F.

The 50% formaldehyde product contained 17,400 ppm formic acid.

EXAMPLE IV

The catalyst was removed from the reactor of Example III. Previously, the tube had been exposed to air so no further air pretreatment was required. The reactor was purged with nitrogen for 15 minutes.

Hydrogen sulfide (100%) was passed through the reactor for 5 minutes and then it was blocked in for 2 hours at a temperature of 600°F. Again the reactor was purged with nitrogen for 15 minutes. Then air was passed through for 19 hours or overnight at the end of which time there was no evidence of sulfur dioxide in the effluent by either odor or lead acetate solution. The reactor tube was reloaded with catalyst and production of formaldehyde was resumed. The 50 wt.% formaldehyde solution contained less than 20 ppm formic acid.

The present invention is particularly advantageous in that formaldehyde can be produced in a carbon steel reactor instead of the stainless steel reactor heretofore required in the art. The formaldehyde product contains less than 400 ppm formic acid, and generally less than 50 ppm of formic acid.

Numerous modifications and variations of the present invention are possible in light of the above teachings and, therefore, within the scope of the appended claims the invention may be practised otherwise than as particularly described.

What is claimed is:

1. In a process for producing formaldehyde by the oxidation of methanol in a carbon steel reactor, the improvement comprising:

treating the surface of the carbon steel reactor prior to said oxidation of methanol to formaldehyde with a passivating amount of a member selected from the group consisting of (a) a mixture of oxygen and sulfur dioxide and (b) hydrogen sulfide, said treatment with hydrogen sulfide being effected in the absence of oxygen on an oxidized carbon steel surface, said treatment being effected at a temperature and for a time to passivate the carbon steel surface with respect to the production of formic acid.

2. The process of claim 1 wherein the treatment is effected at a temperature from about 300°F to about 800°F.

3. The process of claim 2 wherein the treatment is effected with hydrogen sulfide.

4. The process of claim 3 wherein the treatment is effected at a temperature from about 500°F to about 650°F.

5. The process of claim 3 wherein the hydrogen sulfide is employed in admixture with an inert gas.

6. The process of claim 2 wherein the treatment is effected with a mixture of sulfur dioxide and oxygen.

7. The process of claim 6 wherein the treatment is effected at a temperature from about 500°F. to about 650°F.

8. The process of claim 7 wherein volume ratio of oxygen to sulfur dioxide is from 4:1 to 40:1.

9. The process of claim 4 wherein the treatment is effected with a gas containing at least 1.5%, by volume, of hydrogen sulfide.

10. The process of claim 9 wherein the treatment is effected for a time of at least 0.5 hour.

11. The process of claim 8 wherein the treatment is effected for at least 1 hour.

* * * * *